Figure 3:
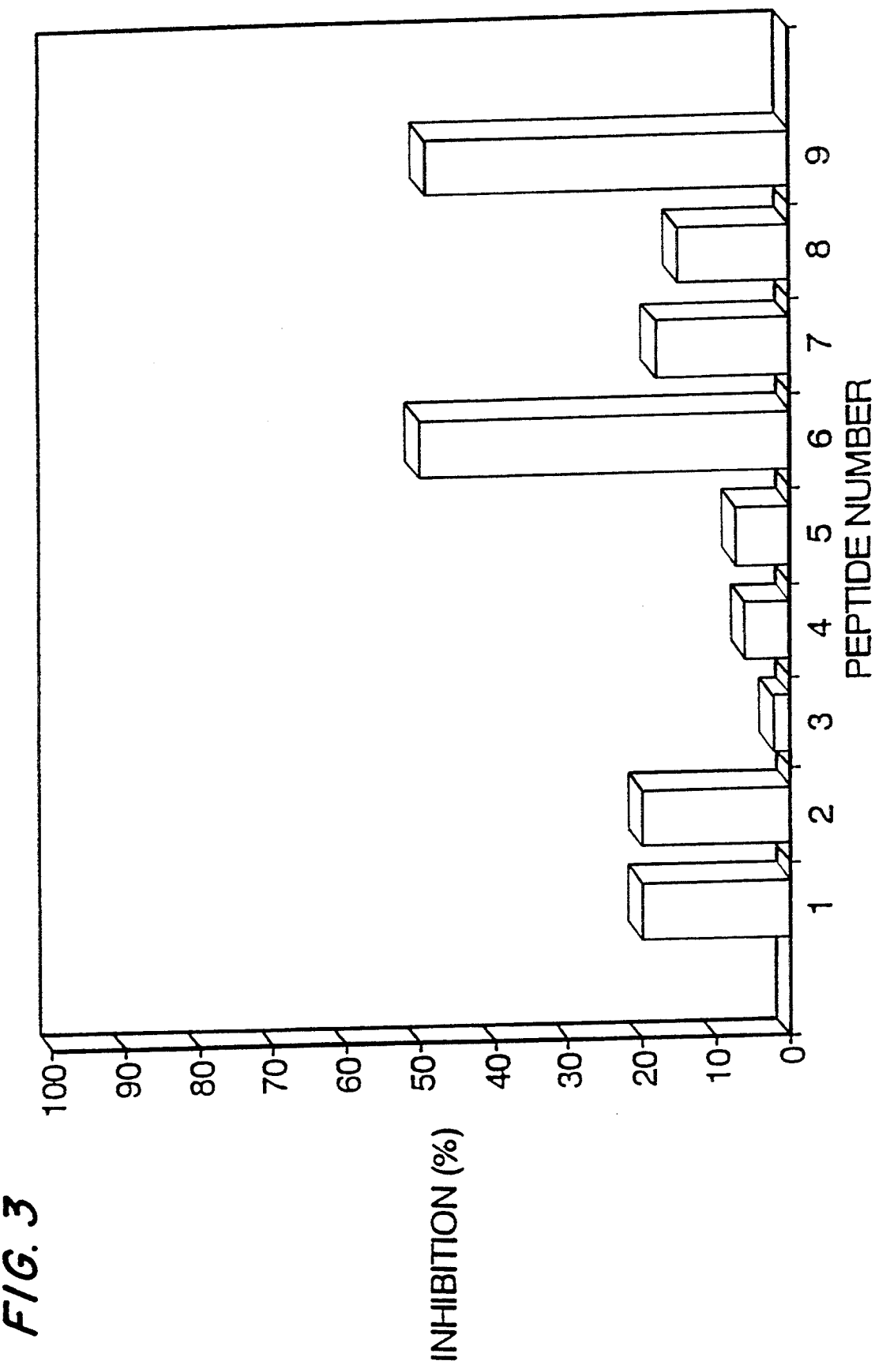

United States Patent [19]

Metcalfe et al.

[11] Patent Number: 5,449,669

[45] Date of Patent: Sep. 12, 1995

[54] IGE-BINDING EPITOPES OF A MAJOR HEAT-STABLE CRUSTACEAN ALLERGEN DERIVED FROM SHRIMP

[75] Inventors: Dean D. Metcalfe; Brian M. Martin, both of Bethesda, Md.; Pillarisetti V. S. Roa, Bangalore, India

[73] Assignee: The United States of America represented by the Dept. of Health and Human Services, Washington, D.C.

[21] Appl. No.: 149,809

[22] Filed: Nov. 10, 1993

[51] Int. Cl.$^6$ .......................... C07K 7/06; C07K 7/08; A61K 38/08; A61K 38/10
[52] U.S. Cl. ....................................... 514/13; 514/15; 530/326; 530/328
[58] Field of Search .................. 530/328, 326; 514/13, 514/15

[56] References Cited

PUBLICATIONS

Nagpal et al. "Isolation and characterization of heat-stable allergens from shrimp (Penaeus indicus)", J. Allergy Clin. immunol., 83:26–36 (1989).

O'Hehir and Lamb "Strategies for modulating immunoglobulin E synthesis", Clin. Exp. Allergy, 22:7–10 (1992).

Lipman et al. "Rapid and Sensitive Protein Similarity Searches", Science, 227:1435–1441 (1985).

Greaser et al. "Reconstitution of Troponin Activity from Three Protein Components", J. Biol. Chem., 246(13):4226–4233 (1971).

Bradford "A Rapid and Sensitive Method for the Quantitation of Microgram . . . ", Anal Biochem. 72:248–254 (1976).

Dubois et al. "Colorimetric method for Determination of Sugars and Related Substances", Anal Chem., 28:350–356 (1956).

Laemmli "Cleavage of Structural Proteins during the Assembly of the Head of Bacteriophage T4", Nature, 227:680–685 (1970).

Hoffman et al. "The Major Heat Stable Allergen of Shrimp", Annals of Allergy, 47:17–22 (1981).

Subba Rao et al. Abstract, Immunol. Methods, 57:71 (1983).

Primary Examiner—Jill Warden
Assistant Examiner—Carol A. Salata
Attorney, Agent, or Firm—Foley & Lardner

[57] ABSTRACT

A major heat-stable shrimp allergen is characterized as a 34 kDa protein corresponding to shrimp tropomyosin. Two IgE binding epitopes of this allergen have the sequences FLAEEADRK (SEQ ID NO: 1) and MQQLENDLDQVQESLLK (SEQ ID NO: 2), respectively. Surprisingly, both antigenic and allergenic activities of the allergen were found to be associated with these two peptide fractions. A-a-id antibodies recognized this allergen as well as a homologous 34 kDa allergen from lobster, prawn and crab, indicating that these antibodies recognize major cross-reacting IgE binding epitopes common to crustacea. The two epitopes are useful in the diagnosis and/or treatment of allergies, particularly in the desensitization of individuals that are allergic to shrimp and other crustacea. Variants and subfragments of the two epitopes display allergenicity, as assessed by reaction with allergen-specific IgE obtained from shrimp-sensitive patients.

20 Claims, 6 Drawing Sheets

FIG. 1

| Source | Amino acid residues | |
|---|---|---|
| | 50————————66 | 153————161 |
| Shrimp | M-Q-Q-L-E-N-D-L-D-Q-V-Q-E-S-L-L-K | F-L-A-E-E-A-D-R-K |
| Dros | I-Q-T-V-E-N-E-L-D-Q-T-Q-E-A-L-T-L | F-L-A-E-E-A-D-K-K |
| Rat | L-K-G-T-E-D-E-L-D-K-Y-S-K-A-L-K-D | H-I-A-E-D-A-D-R-K |
| Chick | L-K-G-T-E-D-E-V-E-K-Y-S-K-S-V-K-D | H-I-A-E-E-A-D-R-K |
| Rabbit | L-R-A-S-E-D-E-R-D-R-V-L-K-E-L-H-K | H-I-A-E-E-S-D-R-K |
| Human | L-K-G-T-E-D-E-L-D-K-Y-S-K-A-L-K-D | H-I-A-E-E-A-D-R-K |

FIG. 2

```
  1    M D A I K K K M Q A M K B D K D G A L E
 21    R A L B C E Q E A R D A N T R A E K A E
                                    ⊢―― S ――
 41    E E A R Q L Q K K I Q T V E N E L D Q T
       ―A―V―H―E――――⊣ ―R―M―― Q―L ―――― D ――――― V
 61    Q E A L T L V T G K L E E K N K A L Q N
       ――― S ―― L―K―A―N―I―Q ―― V ―――⊣―D ――――― S ―
 81    A E S E V A A L N R R I Q L L E E D L E
       ――― G ―――――――――――――――――――――――――――――――
101    R S E E R L G S A T A K L S·E A S Q A A
       ―⊣                         ⊢―A―――――――――
121    D E S E R A R K I L E N R A L A D E E R
       ―――――――――――――――――――⊣
141    M D A L E N Q L K E A R F L A E E A·D K
                                   ⊢―――――― R
161    K Y D E V A R K L A M V E A D L E R A E
       ―――――――――――⊣                         ⊢―
181    E R A E Q G E N K I V E L E E E L R V V
       ――――― T ――― S ―――――――――――――――――――――――
201    G N N L K S L E V S E E K S N Q R E E E
       ―――――――――――⊣          ⊢―――――――――――――――
221    Y K N Q I K T L N T R L K E A E A R A E
       ―――――――――⊣                          ⊢―
241    F A E R S V Q K L Q K E V D R L E D D L
       ―――――⊣                            ⊢―E―
261    V L E K E R Y K D I G D D L D T A F V E
       ―N ―――――― K ――――― Q ⊣
281    L I L K E
```

IGE-BINDING EPITOPES OF A MAJOR HEAT-STABLE CRUSTACEAN ALLERGEN DERIVED FROM SHRIMP

BACKGROUND OF THE INVENTION

This invention relates to epitopes of a major heat-stable shrimp allergen and, more particularly, to the use of these epitopes to desensitize individuals that are allergic to shrimp and other crustacea.

Crustacea are among the foods most frequently associated with IgE-mediated type I hypersensitive reactions in individuals allergic to food. Nagpal et al., *J. Allergy Clin. Immunol.* 83:26 (1989), have characterized two major allergens from marine shrimp, *Penaeus indicus*. Both are heat-stable. The first, designated SA-I, has an apparent molecular weight of 8.2 kd. The second, designated Sa-II, has an apparent molecular weight of 34 kd and contains 301 amino acid residues.

Either the entire antigen or allergenic epitopes thereof can be used for desensitization of an allergenic individual. It is preferable to use only allergenic epitopes rather than an entire antigen when desensitizing an individual with a food allergy, since this minimizes the possibility of a severe adverse reaction during the desensitization treatment. While SA-I and SA-II have been indicated as being major heat-stable shrimp allergens, there is no suggestion that either of these allergens contains within its sequence allergenic epitopes, or what these allergenic epitopes might be.

SUMMARY OF THE INVENTION

It is therefore an object of the present invention to provide allergenic epitopes of a shrimp allergen.

It is a further object of the invention to provide allergenic epitopes that can desensitize an individual to the allergenic components of shrimp and other crustacea without producing a severe, adverse reaction in the individual during desensitization.

These and other objects of the invention are achieved by a peptide selected from the group consisting of FLAEEADRK (SEQ ID NO: 1), MQQLENDLDQVQESLLK (SEQ ID NO: 2), and variants thereof having allergenic activity. In a preferred embodiment a peptide variant inhibits the binding to crustacea tropomyosin of crustacea tropomyosin-specific IgE antibodies by at least 45%.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIG. 1 is a comparison of amino acid residues in the regions 50–66 and 153–161 for tropomyosin from various species. SEQ ID NOS 1, 2 and 16–23 are shown in this Figure.

FIG. 2 is a comparison of amino acid sequences of peptide fragments of Pen i I (SEQ ID NO: 24) with the deduced amino acid sequence of the α-chain of *D. melanogaster* tropomyosin.

FIG. 3 is a graphic showing inhibition of binding of shrimp-specific IgE antibodies to tropomyosin by tryptic peptides of tropomyosin.

FIG. 4 are AB-microELISA inhibition curves for purified allergenic peptide 6 and peptide 9. Triangles represent results with normal sera and circles represent results with shrimp-sensitive sera. Open symbols represent results for peptide 6 and solid symbols represent results for peptide 9.

FIG. 5 are AB-microELISA inhibition curves for Pen i I and tropomyosin. Triangles represent results with normal sera and circles represent results with shrimp-sensitive sera. Open symbols represent results for Pen i I and solid symbols represent results for shrimp tropomyosin.

FIG. 6 is a bar graph showing allergenic cross-reactivity between tropomyosins from different species. The open (top) bar represents incubation with 0.1 μg/ml of tropomyosin, the solid (middle) bar represents incubation with 10 μg/ml of tropomyosin and the stippled (bottom) bar represents incubation with 100 μg/ml of tropomyosin from the respective species. The results are presented as percent inhibition of the binding of shrimp-specific IgE antibodies to tropomyosin in the presence of each inhibitor.

DETAILED DESCRIPTION OF THE PREFERRED EMBODIMENTS

It has been discovered that the major heat stable shrimp allergen that provokes IgE-mediated, immediate.-type hypersensitivity reactions following the ingestion of cooked shrimp is a 34 kDa heat-stable protein which contains 300 amino residues and is rich in glutamic and aspartic acid. This allergen has been designated "SA-II." A comparison between (A) amino acid sequences of different peptides, totalling 150 residues, generated by proteolysis of SA-II and (B) sequences generated with MicroGenie protein database (release 91.1) revealed an 86% homology of Sa-II with the muscle protein tropomyosin from *Drosophila melanogaster*. Isolation of tropomyosin from uncooked shrimp (*Penaeus indicus*) and comparison of its physicochemical and immunochemical properties with SA-II has confirmed that the latter is shrimp tropomyosin. In accordance with the International Convention for naming of allergens, SA-II has been assigned the name Pen i I.

The similarities observed between shrimp tropomyosin and Pen i I were striking. Both tropomyosin and Pen i I had the same apparent molecular weight and focussed in a pI range of 4.8–5.4. In the presence of 6M urea, the mobility of both Pen i I and shrimp tropomyosin shifted to an apparent molecular weight of 50 kDa, a characteristic property of tropomyosins in general. In addition, shrimp tropomyosin bound to specific IgE antibodies in the sera of shrimp-sensitive patients, as assessed by competitive ELISA inhibition and Western blot analysis.

Tryptic maps of both Pen i I and shrimp tropomyosin, as obtained by reverse phase HPLC, were superimposable. Amino acid sequencing of Pen i I revealed the presence of repeating heptads of the form $(a\text{-}b\text{-}c\text{-}d\text{-}e\text{-}f\text{-}g)_n$, where a and d are non-polar residues, a unique feature of tropomyosins generally.

In accordance with the present invention, identification and characterization of cross-reacting IgE binding epitopes is used to elucidate the structural and molecular basis of cross-reactivity between allergens from different crustacean species, and to clarify interactions between allergens and the immune system. While many immunological studies have focussed on the analysis of antigenic determinants on proteins, characterization of the allergenic (IgE binding) determinants has proceeded more slowly. To date, hardly any comparisons of allergenic and antigenic determinants have been made, and there are few studies on the identification of allergenic determinants using allergen-specific IgE present in patient sera.

In order to study and identify the allergenic determinants of Pen i I, trypsin digestion was used. Trypsin digestion of Pen i I produced peptide fragments less than 2 kDa. Two of these fragments displayed allergenic activity as determined by IgE binding with a dot blot immunoassay using polyclonal sera from shrimp-sensitive patients. The two fragments each individually blocked about 45% of the binding of allergen-specific IgE to tropomyosin. The fractions of Pen i I that bind to allergen-specific IgE antibodies in the sera of shrimp-sensitive patients have been purified and sequenced and are denoted peptide 6 (SEQ ID NO: 1) and peptide 9 (SEQ ID NO: 2), respectively. Their sequences are shown in Table I. Surprisingly, both antigenic and allergenic activities of Pen i I were found to be associated with these two peptide fractions, that is, the IgG and IgE binding epitopes were identical.

TABLE I

| Peptide | Residues* | Sequence |
| --- | --- | --- |
| Peptide 6 (SEQ ID NO: 1) | 153-161 | F L A E E A D R K |
| Peptide 9 (SEQ ID NO: 2) | 50-66 | M Q Q L E N D L D Q V Q E S L L K |

*Residue number from alignment with amino acid sequence of *D. melanogaster* tropomyosin.

In keeping with standard polypeptide nomenclature, the following abbreviations shown below for amino acid residues are used.

| TABLE OF CORRESPONDENCE | | | | | |
| --- | --- | --- | --- | --- | --- |
| Ala | A | Alanine | Leu | L | Leucine |
| Arg | R | Arginine | Lys | K | Lysine |
| Asn | N | Asparagine | Met | M | Methionine |
| Asp | D | Aspartic acid | Phe | F | Phenylalanine |
| Cys | C | Cysteine | Pro | P | Proline |
| Glu | E | Glutamic Acid | Ser | S | Serine |
| Gln | Q | Glutamine | Thr | T | Threonine |
| Gly | G | Glycine | Trp | W | Tryptophan |
| His | H | Histidine | Tyr | Y | Tyrosine |
| Ile | I | Isoleucine | Val | V | Valine |

Following trypsin digestion the allergenic epitopes were further characterized using anti-antiidiotopic (a-a-id) antibodies prepared from idiotypic (id) antibodies. Id antibodies are antibodies having specific antigenic determinants in the variable domain. Due to the presence of these specific antigenic determinants, id antibodies can be used to identify epitopes. Immunization with id antibodies induces anti-idiotypic (a-id) antibodies which can compete with the native allergen for binding to id antibodies. A-id antibodies resemble the conformation of the original immunogen, that is, they resemble epitopes and do not recognize them. A-id antibodies are mirror images of antigen.

In order to characterize or identify the epitopes and anti-antiidiotypic (a-a-id) antibody. An a-a-id antibody is an antibody which recognizes the epitope. In accordance with the present invention, a-a-id antibodies are used to confirm cross-reacting allergenic determinants of pen i I, particularly the IgE binding epitopes. A-a-id antibodies raised against Pen i I-specific human id antibodies recognized not only shrimp tropomyosin, but also peptide 6 and peptide 9, further indication that these peptides represent major IgE binding epitopes of shrimp tropomyosin. The successful recognition by the a-a-id antibodies demonstrates that a-a-id antibodies can be used effectively as a tool in epitope characterization.

The a-a-id antibodies also recognized a 34 kDa allergen from lobster, prawn and crab. The 34 kDa cross-reacting allergens from related crustaceans are capable of inhibiting more than 90% of binding of Pen i I specific a-a-id antibodies to Pen i I, emphasizing that these antibodies recognize major cross-reacting IgE binding epitopes common to crustacea.

The high degree of cross-reactivity among the crustacea means that peptide 6 and peptide 9 have utility beyond their use in diagnosis and/or treatment of shrimp allergies. Variants of peptide 6 and peptide 9 that retain allergenicity as assessed by reaction with allergen-specific IgE obtained from shrimp-sensitive patients as described herein are also useful in diagnosis and treatment. The high degree of cross-reactivity also explains why individuals allergic to shrimp often complain of adverse reactions following ingestion of other related crustaceans such as lobster, prawn, crab and other shell fish.

The allergenic epitopes according to the present invention appear to correspond to highly conserved regions of crustacean tropomyosin. Identification of these conserved regions means that a wide range of allergies can be diagnosed and/or treated with a single composition containing a synthetic peptide corresponding to a portion of one or both of the two binding regions identified in accordance with the present invention. These synthetic peptides should be useful in the diagnosis and treatment of individuals sensitive not only to shrimp allergens in particular but also to crustacea and shellfish in general. Indeed, they may prove useful in the diagnosis and/or treatment of individuals sensitive to any atopic allergen.

The IgE binding epitopes of Pen i I occur in the regions of amino acid residues 50-66 and amino acid residues 153-161. FIG. 1 presents a comparison of each of these two amino acid sequences with its corresponding amino acid sequence in tropomyosins from unrelated, i.e., phylogenetically distinct, species. Tropomyosins from human (SEQ ID NOS 18 and 21) and other vertebrate sources (SEQ ID NOS 18 and 19, 20 and 21, and 22 and 23) have no homology between amino acids 50-66 of shrimp tropomyosin (SEQ ID NO: 2), and only about 70% homology in the region corresponding to amino acids 153-161 (SEQ ID NO: 1), and display a general lack of allergenic cross-reactivity with tropomyosin from shrimp. Tropomyosin from *D. melanogaster*, on the other hand, has 50% homology in the region of amino acids 50-66 (SEQ ID NO: 16) and 95% homology in the region of amino acids 151-163 (SEQ ID NO: 17).

Focussing on the smaller region of amino acids 155-161, a greater homology is revealed for tropomyosins from different sources, as shown in FIG. 1. Among the species shown in FIG. 1, however, cross-reactivity occurs only with tropomyosin from *D. melanogaster*. A lack of allergenic cross-reactivity for tropomyosins from sources other than *D. melanogaster* indicates that residues 153 and 154 (phenylalanine and leucine, respectively) are critical amino acids involved in binding to IgE antibodies or class II MHC molecules. Presence of these crucial residues in *D. melanogaster* tropomyosin explains its high degree of cross-reactivity with shrimp tropomyosin.

Sequence data show that the IgE binding sequences corresponding to peptide 6 (SEQ ID NO: 1) and peptide 9 (SEQ ID NO: 2) are localized on different regions of shrimp tropomyosin. Release of histamine by basophils or mast cells requires cross-linking of cell-bound IgE by specific antigen molecules. Such cross-linking can be achieved either by two repeating epitopes or by two structurally different epitopes localized on different regions of an allergen. The latter situation appears to exist with respect to shrimp tropomyosin.

Peptide 6 and peptide 9 can be used in the diagnosis and treatment of allergies to shrimp and related crustacea, in accordance with generally recognized principles. For example, strategies for modulating immunoglobulin E synthesis are taught by O Hehir and Lamb, *Clin. Exp. Allergy* 22:7 (1992), and synthetic approaches to vaccines for infectious and autoimmune diseases are provided by Sela and Arnon, *Vaccine,* 10:991 (1992). When the peptides are used in a desensitization treatment, it may be desirable to fuse the peptide to a immunocarrier, i.e., a substance, usually a polypeptide or protein, which is critical for the efficient interaction between T and B cells for the induction of an immune response against a small antigen that is attached to it.

In addition to peptide 6 and peptide 9 per se, a wide variety of polypeptides containing the epitopes embodied in peptide 6 and peptide 9 are useful in accordance with the present invention. Based on the nucleotide sequences in Table I, polypeptide molecules can also be produced which contain variations of the naturally-occurring epitopes, or which contain the naturally-occurring epitopes and variations thereof as part of a longer sequence. These polypeptide molecules are referred to here generically as "peptide 6 or peptide 9 variants" and include, for example, fragments and muteins or peptide 6 and peptide 9, as well as larger molecules that correspond to a portion of Pen i I that consists essentially of peptide 6 or peptide 9, respectively.

In this regard, a molecule that consists essentially of peptide 6 or peptide 9 is one that can safely desensitize individuals to the tropomyosin allergen without causing a severe adverse reaction. A severe adverse reaction is characterized by systemic manifestations, such as severe generalized pruritus, vomiting or hypotension, and can be readily recognized by a person having ordinary clinical skill. A "peptide 6 or 9 mutein" is a polypeptide that is homologous to peptide 6 (SEQ ID NO: 1) or 9 (SEQ ID NO: 2), respectively, and that retains the basic functional attribute—namely, the allergenic activity—of peptide 6 or 9. For purposes of this description, "homology" between two sequences connotes a likeness short of identity indicative of a derivation of the first sequence from the second. In particular, a polypeptide is "homologous" to peptide 6 or 9 if a comparison of amino-acid sequences between the polypeptide and peptide 6 or 9 reveals an identity of greater than 70%. Such a sequence comparison can be performed via known algorithms, such as the one described by Lipman and Pearson, *Science* 227:1435 (1985), which are readily implemented by computer. A peptide 6 or peptide 9 fragment is a molecule in which one or more amino acids, exclusive of amino acids 153 and 154 of peptide 6, are truncated from peptide 6 or peptide 9, respectively. Peptide 6 or 9 muteins and fragments can be produced, in accordance with the present invention, by known de novo-synthesis techniques. Peptides also can be produced by a variety of other conventional techniques, such as by t-boc peptide synthesis, f-moc peptide synthesis, enzymatic synthesis and recombinant DNA methodology.

Also exemplary of peptide 6 and peptide 9 variants within the present invention are molecules that are longer than peptide 6 or peptide 9, respectively, but that contain peptide 6 (SEQ ID NO: 1) or peptide 9 (SEQ ID NO: 2) or a mutein thereof within the longer sequence. The portion of the sequence of such molecule other than that portion of the sequence corresponding to peptide 6 or 9 may or may not be homologous to the sequence of Pen i I. If it is homologous with Pen i I, it is not coincident with the sequence of Pen i I. It will be appreciated that peptides shorter than peptide 6 and peptide 9, respectively, that retain allergenic activity are likewise included within the scope of the present invention. Thus, peptide 6 and 9 variants may be of the same length or longer and shorter than the peptide 6 or 9, respectively, and also includes sequences in which there are amino acid substitutions of the parent sequence. These variants must retain the allergenic activity of peptide 6 or 9.

Whether a synthetic polypeptide produced based on the sequences shown in Table I (SEQ ID NOS. 1 and 2) retains the allergenic activity of peptide 6 or 9 can be determined routinely by means of an assay for a allergenic activity. More particularly, allergenic activity may be assessed by determining the degree of IgE binding with an immunoassay using sera from shrimp-sensitive patients. Allergenic activity is defined in terms of the ability of the peptides to evoke positive skin reactions in patients sensitive to crustaceans, to bind to IgE antibodies in the sera of allergic patients using an immunoassay and to inhibit binding of tropomyosin-specific IgE antibodies to tropomyosin by 45%.

The level of inhibition of binding of tropomyosin-specific IgE antibodies to tropomyosin can be assessed by running two immunoassays in parallel. Tropomyosin can be bound to a support and acts as a binding ligand. For example, one hundred microliters of a 5 $\mu$g/ml solution of tropomyosin can be added to each microtiter well. A control sample, for example, 0.1 ml of 1:10 diluted patient serum containing tropomyosin-specific IgE antibodies, is brought into contact with a first tropomyosin-containing support and allowed to react. After washing away excess tropomyosin-specific IgE antibodies, the support is contacted with a second antibody, e.g., an anti-human Ig enzyme conjugate. The level of binding is visualized and quantitated by providing the substrate for the enzyme.

A test sample containing the putative peptide variant in addition to the same amount of patient sera containing tropomyosin-specific IgE antibodies as in the control sample is brought into contact with a second tropomyosin-containing support identical to the first support and allowed to react. For example, the sera of shrimp-sensitive patients diluted 1:10 may be preincubated with 100–1000 picomoles/ml of each peptide. After washing away excess tropomyosin-specific IgE antibodies, the support is contacted with the same second antibody. The level of binding again is visualized and quantitated by providing the substrate for the enzyme. Any decrease in the level of binding of second antibodies to this second support vis-a-vis the level of binding of second antibodies to the first support is the result of binding of the putative peptide to sites on the binding ligand. A decrease in the level of binding of about 45% identifies peptides in accordance with the present invention.

The present invention can be further understood from the following illustrative examples.

EXAMPLE 1

IgE antibodies from sera of shrimp-sensitive patients

Sera were obtained from four patients with documented immediate hypersensitivity reactions after ingestion of cooked shrimp. All of them had positive prick skin test reaction to shrimp antigen extract and had serum IgE antibodies specific for the major shrimp allergen, pen i I. Shrimp allergen (Pen i I)-specific antibodies were determined by avidin-biotin microELISA (AB-microELISA) according to the method of Subba Rao et al., *J. Immunol. Methods,* 57:71 (1983). Sera collected from three normal subjects with no history of atopy served as negative controls.

EXAMPLE 2

Isolation and purification of Pen i I

The major shrimp allergen Pen i I was purified from boiled aqueous extracts of fresh unshelled shrimp, Penaeus indicus, according to the method of Nagpal et al., *J. Allergy Clin. Immunol.* (1989), supra, the contents of which are incorporated herein by reference. The homogeneity of the preparation was verified by SDS-PAGE and crossed immuno-electrophoresis. Allergenicity was established by AB-microELISA and Western blotting for allergen-specific IgE antibodies as described in Nagpal et al., *J. Allergy Clin. Immunol.* (1989), supra.

EXAMPLE 3

Preparation and sequencing of peptide fragments from Pen i I and comparison to tropomyosin from *D. melanogaster*

(a) Tryptic digestion.

Reduced and carboxymethylated protein, either Pen i I or tropomyosin, was subjected to limited proteolytic digestion with TPCK trypsin (enzyme-substrate ratio 1:500) for one hour at 37° C. with intermittent agitation. The digestion was stopped by freezing the sample in liquid nitrogen. The reaction mixture was subjected to HPLC on a Zorbax ODS column using a Shimadzu CR-6A HPLC system. A linear gradient of 0–100% Solvent B (Solvent A: 0.1% trifluoroacetic acid; Solvent B: 70% acetonitrile in Solvent A) at the rate of 1 ml/min over 50 minutes was used to elute the peptides which were monitored by measuring the absorbance at 220 nm. Each peak was manually collected, dried in vacuo and redissolved in distilled water.

Individual peak fractions were collected and the IgE binding activity of each fraction was assessed by dot blot immunoassay using the sera of shrimp-sensitive patients. Fractions 6 and 9, which eluted with a retention time of 25.8 and 34.6 minutes, respectively, were found to bind to IgE antibodies in the sera of shrimp-sensitive patients. Fractions 6 and 9 did not react with sera from normal subjects.

Before sequencing, peptides from the trypsin digests of Pen i I were repurified using the narrow bore procedure described below for the separation of peptides generated by Asp N and Lys C digestion of Pen i I. Rechromatography of fractions 2, 6 and 9 on the narrow bore Zorbax column yielded several pure peptides.

Amino acid sequence determination was done using either an Applied Biosystem Model 470 A sequencer with an on-line PTH analyzer or a Milligen Biosearch Model 6600 Prosequencer. Samples for the Model 6600 were coupled to Sequelon AA following the manufacturer's protocols. Homology searches of protein data base were done using MicroGenie software and the latest database from PC/Gene. The amino acid sequence of peptides from Pen i I revealed greater than 98% identity with the deduced amino acid sequence of a cDNA for *D. melanogaster* tropomyosin.

(b) Endopeptidase Asp N and Lys C digestion.

In order to verify that Pen i I is tropomyosin, Pen i I (approximately 50 μg) was digested with Asp N and Lys C (1 μg in 50 mM Tris, pH 8.5) at 30° C. for 16 hours. The resulting peptides were separated on a Zorbax C-8 column (2.1 mm × 150 mm) using a linear gradient from 2% B to 50% B over 60 minutes at a flow rate of 200 μl/min (Solvent A consisted of 0.12% TFA in water and Solvent B 0.1% TFA in acetonitrile). Peptides were monitored at both 225 nm and 280 nm using a Beckman System Gold HPLC and collected manually. The sequence of several of these peptides confirmed that Pen i I is tropomyosin, although the degree of homology with *D. melanogaster* dropped to 86% (129 of 150 amino acids determined).

The sequence of several of the peptides produced by trypsin, Asp N and Lys C digestion is shown in Table II. A comparison of amino acid sequences of peptide fragments of Pen i I (SEQ ID NO: 24) with the deduced amino acid sequence of the α-chain of *D. melanogaster* tropomyosin is shown in FIG. 2.

TABLE II

| Residue Number* | Peptide Sequence |
|---|---|
| | Trypsin Peptides |
| 36–48 (SEQ ID NO: 3) | A E K S E E A E V H E L Q K |
| 50–66 (SEQ ID NO: 2) | M Q Q L E N D L D Q V Q E S L L K |
| 77–88 (SEQ ID NO: 4) | L A E A S Q A A D E S E R |
| 153–167 (SEQ ID NO: 5) | F L A E E A D R K Y D E V A R |
| 161–167 (SEQ ID NO: 6) | K Y D E V A R |
| 214–226 (SEQ ID NO: 7) | S N Q R E E E Y K N Q I K |
| 239–244 (SEQ ID NO: 8) | A E F A E R |
| | Asp N Peptides |
| 58–74 (SEQ ID NO: 9) | D Q E S L L K A N I Q L V E K |
| 77–94 (SEQ ID NO: 10) | D K A L S N A E G E V A A L N R R I Q L |
| 180–195 (SEQ ID NO: 11) | E E R A E T G E S K I V E L E |
| 258–269 (SEQ ID NO: 12) | D L V N E K E K Y K Q |
| | Lys C Peptides |
| 49–59 (SEQ ID NO: 13) | R M Q Q L E N D L D Q |
| 77–101 (SEQ ID NO: 14) | A L S N A E G E V A A L N R R I Q L L E E D L E |

TABLE II-continued

| Residue Number* | Peptide Sequence |
| --- | --- |
| 190–205 (SEQ ID NO: 15) | I V E L E E E L R V V G N N L K |

*Residue number from alignment with the amino acid sequence for *D. melanogaster* tropomysin.

EXAMPLE 4

Isolation and purification of shrimp tropomyosin and comparison to Pen i I

Tropomyosin was isolated from shrimp according to the procedure of Greaser and Gergely, *J. Biol. Chem.* 246:13 (1971). Fresh shrimp (200 g) were minced thoroughly in a blender and soluble sarcoplasmic proteins were removed by extraction for 5 minutes with a dilute salt solution containing 20 mM KCl, 1 mM KHCO$_3$, 0.1 mM CaCl$_2$ and 0.1M DTT. The suspension was filtered through a cheese cloth and the residue was washed four times with the salt solution.

Two volumes of 95% ethanol were added to the residue and the solution was filtered after 10 minutes. The ethanol extraction was repeated twice and the residue was then washed three times with diethyl ether. Finally, the residue was allowed to dry at room temperature for 2–3 hours. The dried powder was extracted overnight at 22° C. with a high salt solution containing 1M KCl, 25 mM Tris, pH 8.0, 0.1 mM CaCl$_2$ and 1 mM DTT.

After filtering through a cheese cloth, the residue was once again extracted with 1M KCl and the combined extracts were chilled to 4° C. The extract was then subjected to 30–60% ammonium sulphate fractionation. The precipitate was dissolved in 5 mM Tris, pH 7.5 containing 0.1M CaCl$_2$ and 0.1M DTT and dialyzed extensively against the same buffer. Tropomyosin was selectively separated by isoelectric precipitation at pH 4.5–4.7 leaving troponin complex in the supernatant. The precipitate was redissolved in 1M KCl and isoelectric precipitation was repeated three times at pH 4.6. Ammonium sulphate fractionation between 53–60% was used for further purification. The precipitate was dissolved in 10 mM NH$_4$HCO$_3$ buffer, pH 8.0 and dialyzed extensively against the same buffer. Thirty milligrams of tropomyosin was obtained.

Size exclusion chromatography of purified Pen i I and shrimp tropomyosin was performed on a Shimpack Diol-150 column using a Shimadzu LC-6A HPLC system. Sodium phosphate at pH 7.2 (10 mM) containing sodium sulphate (150 mM) was used as the mobile phase at a flow rate of 1 ml/min and the elution of proteins was monitored at 280 nm and 225 nm, respectively. Both Pen i I and shrimp tropomyosin have an apparent molecular weight of 34 kDa.

Protein was determined by the dye binding method of Bradford, *Anal. Biochem.* 72:248 (1976) using crystalline BSA as a standard. The total carbohydrate content of the purified allergen was estimated by phenol sulfuric acid method using glucose as a standard, according to Dubois et al., *Anal. Chem.* 28:350 (1956). Both tropomyosin and Pen i I were devoid of carbohydrate and migrated as a single band with a molecular weight of 34 kDa.

Electrophoresis was carried out at room temperature for two hours at 120 V and 30 mA. After electrophoresis, the gel was fixed in 10% TCA for 30 min and subsequently stained with Coomassie Brilliant Blue R-250. The molecular weight of allergenic proteins was calculated from a standard curve constructed by plotting the mobility of the marker proteins relative to the tracking dye. Both tropomyosin and Pen i I migrated as a single band with an apparent molecular weight of 34 kDa.

Tropomyosins are distinguished by a shift in apparent molecular weight in the presence of 6M urea. Tropomyosins from different sources exhibit a unique migration pattern in the presence of 6M urea, with an apparent molecular weight of 50 kDa. For SDS-PAGE in the presence of urea, 6M urea was included in the resolving gel, the stacking gel and in the sample buffer. Pen i I and shrimp tropomyosin exhibited a similar mobility shift and comigrated.

IEF was performed on 5% polyacrylamide gel plates between pH 3–10 at 2000 V, 50 mA and 30 watts. The gel was calibrated with standard marker proteins (pI 3.5–10). Purified proteins (15 μg) were applied to the gel and subjected to IEF. The proteins were fixed with 10% TCA and stained with Coomassie Brilliant Blue R-250. On IEF, both tropomyosin and Pen i I gave multiple bands in the pI range of 4.8 to 5.4, thus behaving as isoallergens.

EXAMPLE 5

Digestion of shrimp tropomyosin and comparison to Pen i I

Shrimp tropomyosin was completely digested in pronase. Like Pen i I, complete digestion of tropomyosin with pronase resulted in total loss of allergenic activity.

Limited digestion of shrimp tropomyosin with TPCK trypsin for 1 hour resulted in the release of peptides that retained allergenic activity as evidenced by their ability to inhibit 80% of the binding to native tropomyosin of Pen i I-specific IgE antibodies in the sera of shrimp-sensitive patients. Fractionation by reverse phase HPLC on a Zorbax ODS column of the tryptic digests of both shrimp and Pen i I resulted in a set of peptides having HPLC profiles that were superimposable.

Size exclusion chromatography of Pen i I and shrimp tropomyosin peptides was performed as described above for purified protein. Complete digestion of protein was confirmed by SDS-PAGE, carried out with Laemmli's discontinuous buffer system [*Nature* 227:680 (1970)]. The tryptic peptides had molecular weights less than 2 kDa and there was no peak corresponding to native tropomyosin. The possibility that the peptide fractions were contaminated with native undegraded allergen which might have accounted for the observed inhibition was ruled out as native allergen could not be detected either by SDS-PAGE or by Western blot analysis.

EXAMPLE 6

Detection of IgE-binding native allergen and tryptic peptides by immunoblotting

Aliquots of native allergen (Pen i I or tropomyosin) or individual peptide fractions separated by HPLC on reverse phase column were spotted on CNBr-activated nitrocellulose strips and the blots were blocked with blocking buffer (0.5% Tween-20 in PBS, pH 7.4) containing 5% BSA overnight at 4° C. The strips were washed 6 times in rinse buffer (0.05% Tween-20 in PBS, pH 7.4) and incubated with shrimp-sensitive patient sera or sera of three normal subjects overnight at 4° C. with mild agitation. Serum was diluted 1:10 (v/v) with serum diluent buffer (0.5% Tween-20 in PBS, pH 7.4 containing 1% BSA). The strips were washed 6 times with rinse buffer and successively incubated with anti-human IgE-biotin conjugate (diluted 1:1000 with serum diluent buffer) overnight at 4° C. and horseradish peroxidase-avidin conjugate (diluted 1:2000 with serum diluent buffer) for one hour at 370° C. with intermittent washing with rinse buffer. The strips were finally placed in peroxidase chromogenic substrate solution (1 mg/ml of diaminobenzidine and 0.3% $H_2O_2$ in 20 mM citrate phosphate buffer, pH 5.5) to visualize the allergenic peptides.

Immunoblotting was carried out according to the procedure of Towbin et al., *PNAS USA* 76:4350 (1979). Proteins resolved on SDS-PAGE were electrophoretically transferred onto nitrocellulose membranes (0–45µ pore size) using an electroblot transfer system (EC Apparatus Corporation, St. Petersburg, Fla.). The rest of the procedure was the same as described above except for the omission of 1% BSA in the serum diluent buffer. The immunoblot and dot blot assays were performed using sera of four shrimp-sensitive patients and three normal subjects.

The antigenicity of each peptide fraction was assessed by dot blot immunoassay for specific IgG antibodies in the sera of shrimp-sensitive patients and revealed that, among the peptides generated by proteolysis of tropomyosin, only peptide 6 and peptide 9 were antigenic.

The allergenicity of each peptide fraction was also evaluated for its ability to inhibit the binding of Pen i I-specific IgE to native tropomyosin. Polystyrene microtiter wells were coated with shrimp tropomyosin (5.37 µg/ml) and the ability of each peptide separated by reverse-phase HPLC to inhibit the binding of IgE antibodies in the sera of shrimp-sensitive patients to native tropomyosin was evaluated by preincubating the sera with each peptide (100 picomoles/ml).

Among all the peptides generated by proteolysis of Pen i I and tropomyosin, only peptide 6 and peptide 9, which eluted at 25.8 and 34.6 min, respectively, bound to IgE antibodies in the sera of shrimp-sensitive patient. These two peptides displayed a maximum inhibition, as shown in FIG. 3. Peptide 6 and peptide 9 did not react with sera from normal subjects.

Figure 4:
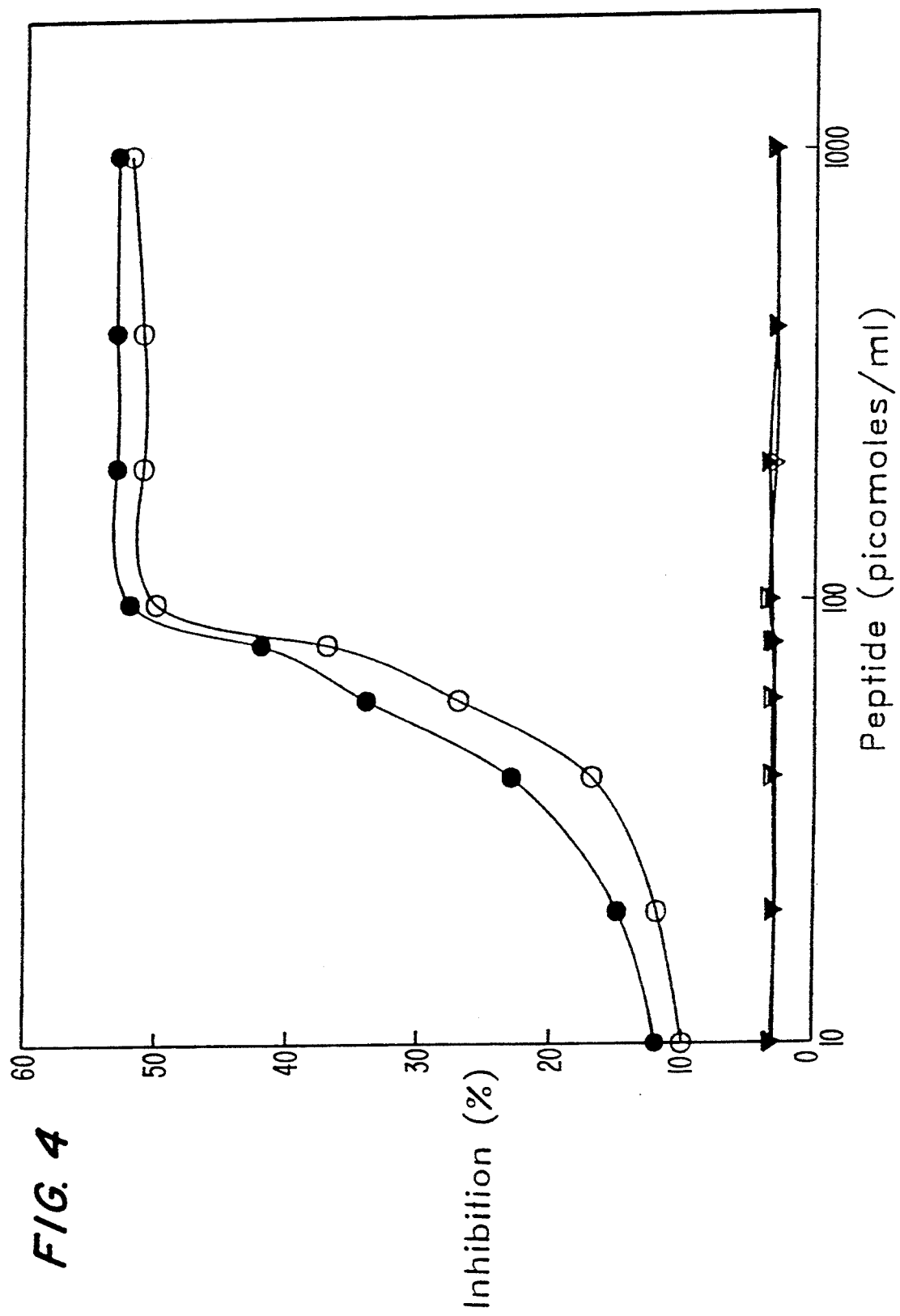

Peptide 6 and peptide 9 had minor contaminants and were purified to homogeneity by manipulation of either the flow rate or the linear gradient of acetonitrile used for elution in HPLC. Shrimp-sensitive patient sera (1:10 dilution) was preincubated with increasing concentrations (10–1000 picomoles/ml) of HPLC-purified tryptic peptides of shrimp tropomyosin (6 or 9) and then added to tropomyosin-coated polystyrene microtiter wells and assayed for binding by AB-microELISA. Both the purified peptides were found to inhibit the binding of Pen i I-specific IgE to tropomyosin in a dose dependent manner with maximum inhibition achieved at a concentration of 100 picomoles/ml, as shown in FIG. 4.

EXAMPLE 7

Quantitation of allergen-specific IgE antibodies
Shrimp allergen (Pen i I or tropomyosin) specific IgE antibodies were determined by AB-microELISA, according to the method described in Nagpal et al. (*J.*

*Immunol.* 1989, supra) and Subba Rao et al., *J. Immunol. Methods* (1983), supra. In competitive ELISA inhibition experiments, test sera diluted 1:10 were preincubated with 0.001 to 100 µg/ml of either native Pen i I or trypsin-digested Pen i I or tropomyosin for one hour at 37° C. prior to incubation with Pen i I or tropomyosin (5 µg/ml) immobilized in polystyrene microtiter wells. The ELISA was performed as described.

Figure 5:
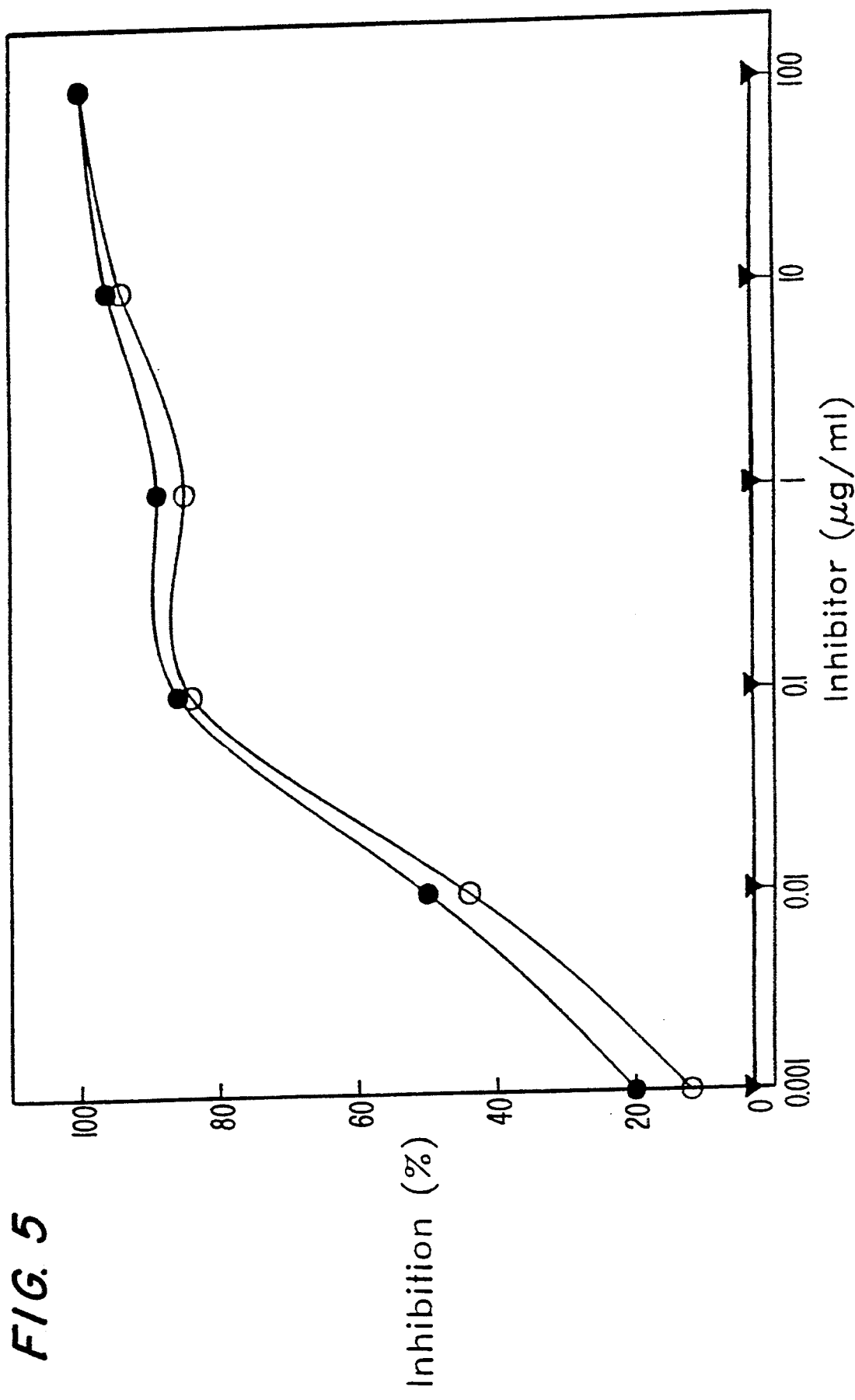

The assay revealed that shrimp tropomyosin was as potent as Pen i I in binding to Pen i I-specific IgE antibodies in the sera of shrimp-sensitive patients. The ability of the tryptic peptides to block the binding of IgE antibodies to the native allergen (Pen i I or tropomyosin) was also assessed. The ELISA inhibition experiments were performed in triplicate and the results represent the average of the three replicates, expressed as percent inhibition in binding to Pen i I or tropomyosin. The results are shown in FIG. 5.

The allergenicity of shrimp tropomyosin was further confirmed by immunoblot analysis using the sera of shrimp-sensitive patients. Preincubation of trypsin-digested Pen i I resulted in 85% inhibition in the binding of IgE antibodies to immobilized native Pen i I.

EXAMPLE 8

Pen i I-specific anti-antiidiotypic (a-a-id) antibodies
Mouse a-a-id antibodies to Pen i I were prepared as described in Nagpal et al., *J. Immunol.* (1989), supra . Dot blot immunoassay proved that these a-a-id antibodies recognized the 34 kDa allergen from shrimp, lobster, prawn and crab. The 34 kDa cross-reacting allergen from related crustaceans was capable of inhibiting more than 90% of binding of Pen i I-specific a-a-id antibodies to Pen i I, confirming that these antibodies recognize the major cross-reacting IgE binding epitopes.

The a-a-id antibodies also were shown to recognize both peptide 6 and peptide 9, further confirming that these peptides represent the major IgE binding epitopes. The results establish that a-a-id antibodies can be effectively used as tools in epitope characterization.

EXAMPLE 9

Figure 6:
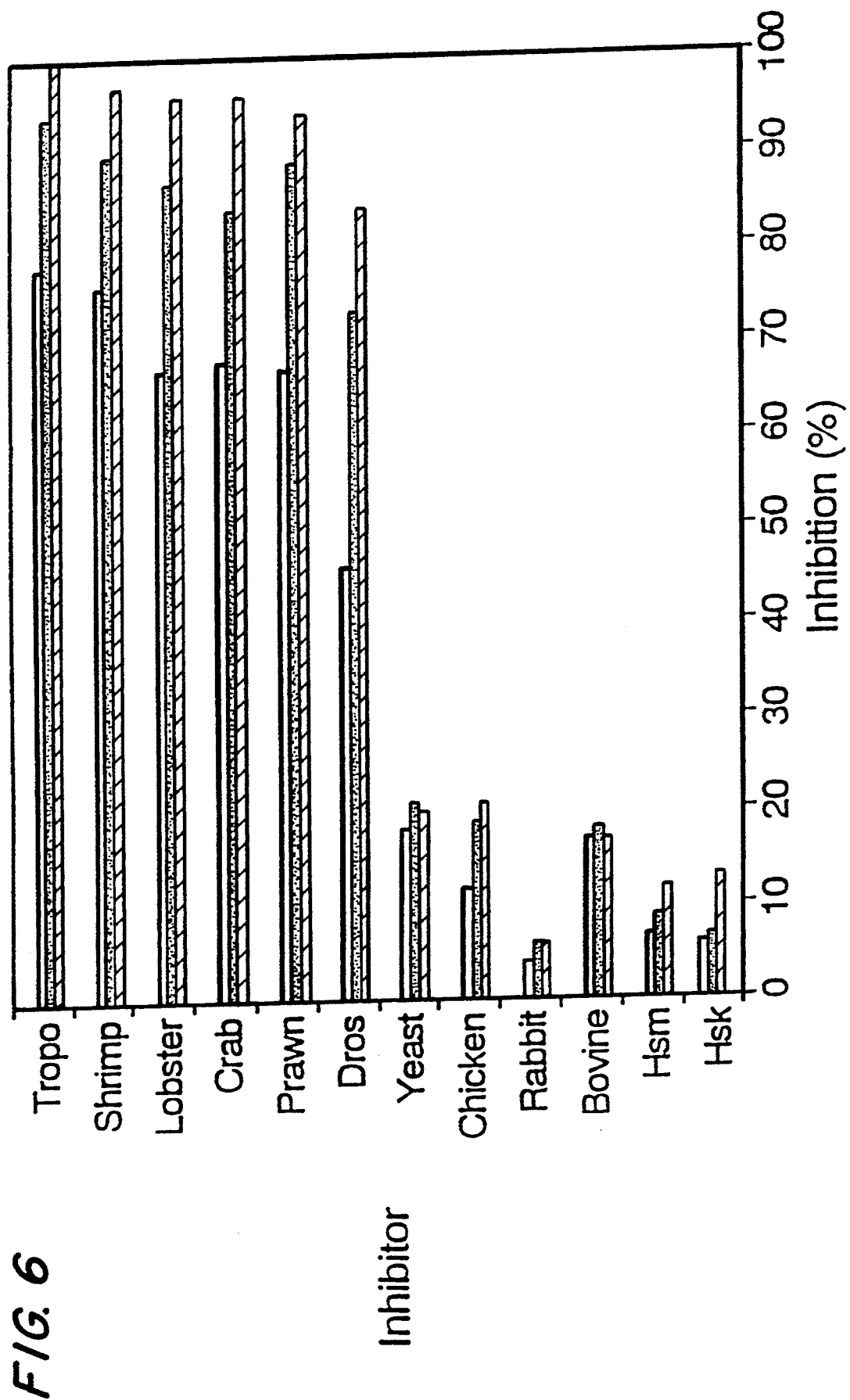

Allergenic cross-reactivity of different tropomyosins
Allergenic cross-reactivity between crude tropomyosin preparations from different crustaceans (shrimp, lobster, prawn, crab), *D. melanogaster*, yeast, chicken, rabbit, bovine and human was assessed by competitive ELISA inhibition assay. Shrimp-sensitive patient serum (1:10 dilution) was preincubated with different concentrations (0.1 to 100 µg/ml) of crude preparations of tropomyosin of the respective species before adding to polystyrene wells coated with shrimp tropomyosin (5 µg/ml). As shown in FIG. 6, binding of IgE antibodies in the serum of a shrimp-sensitive patient to shrimp tropomyosin was blocked up to 95% by tropomyosins from related crustaceans and up to 80% by Drosophila tropomyosin. But tropomyosins from other sources like yeast, chicken, bovine, rabbit and human did not inhibit the binding of shrimp-specific IgE antibodies to shrimp tropomyosin.

EXAMPLE 10

Competitive ELISA assay to assess allergenic activity of a peptide
Tropomyosin is coated onto polystyrene microtiter wells at a concentration of 5 µg/ml for one hour at 37° C. After 5 washes of the allergen coated wells with rinse buffer (0.05% Tween 20 in PBS pH 7.4), the unbound sites are blocked with serum diluent buffer (2% goat serum in rinse buffer for 45 minutes at 37° C. Test sera diluted 1:10 using serum diluent buffer are preincubated with specific quantities of inhibitor (tropomyosin or its tryptic/synthetic peptides) for one hour at 37° C. prior to incubation with immobilized tropomyosin. After washing the wells are incubated with the test sera either with or without the inhibitor for 30 minutes at 37° C. The wells are washed 5 times with rinse buffer and successively incubated with anti-human IgE-biotin conjugate diluted 1:1000 with serum diluent buffer for 30 minutes at 37° C. and horseradish peroxidase-avidin conjugate diluted 1:2000 with serum diluent buffer for 5 minutes at 37° C. with intermittent washing with the rinse buffer. The bound IgE is then visualized and quantitated by adding the peroxidase chromogenic substrate solution (1 mg/ml o-phenylene diamine and 0.3% $H_2O_2$ in 0.2M phosphate buffer pH 7.0). The reaction is then stopped using 2N HCl and the absorbance is read at 492 nm.

To assess the allergenic activity of peptide 6 and peptide 9, the sera of shrimp sensitive patients was diluted 1:10 and preincubated with 100 μl of each peptide (100–100 picomoles/ml) for one hour at 37° C. prior to incubation with tropomyosin immobilized on the polystyrene support. A maximum inhibition of about 45% was obtained at concentrations above 100 picomoles/ml.

While the invention has been described in detail with respect to particular preferred embodiments, it should be understood that such description is presented by way of illustration and not limitation. Many changes and modifications within the scope of the present invention may be made without departing from the spirit thereof, and the invention includes all such modifications.

SEQUENCE LISTING ( 1 ) GENERAL INFORMATION:

( i i i ) NUMBER OF SEQUENCES: 24

( 2 ) INFORMATION FOR SEQ ID NO:1:

( i ) SEQUENCE CHARACTERISTICS:
        ( A ) LENGTH: 9 amino acids
        ( B ) TYPE: amino acid
        ( D ) TOPOLOGY: linear ( x i ) SEQUENCE DESCRIPTION: SEQ ID NO:1:

```
Phe Leu Ala Glu Glu Ala Asp Arg Lys
 1               5
```

( 2 ) INFORMATION FOR SEQ ID NO:2:

( i ) SEQUENCE CHARACTERISTICS:
        ( A ) LENGTH: 17 amino acids
        ( B ) TYPE: amino acid
        ( D ) TOPOLOGY: linear ( x i ) SEQUENCE DESCRIPTION: SEQ ID NO:2:

```
Met Gln Gln Leu Glu Asn Asp Leu Asp Gln Val Gln Glu Ser Leu Leu
 1               5                  10                  15
Lys
```

( 2 ) INFORMATION FOR SEQ ID NO:3:

( i ) SEQUENCE CHARACTERISTICS:
        ( A ) LENGTH: 14 amino acids
        ( B ) TYPE: amino acid
        ( D ) TOPOLOGY: linear ( x i ) SEQUENCE DESCRIPTION: SEQ ID NO:3:

```
Ala Glu Lys Ser Glu Glu Ala Glu Val His Glu Leu Gln Lys
 1               5                  10
```

( 2 ) INFORMATION FOR SEQ ID NO:4:

( i ) SEQUENCE CHARACTERISTICS:
        ( A ) LENGTH: 13 amino acids
        ( B ) TYPE: amino acid
        ( D ) TOPOLOGY: linear ( x i ) SEQUENCE DESCRIPTION: SEQ ID NO:4:

```
Leu Ala Glu Ala Ser Gln Ala Ala Asp Glu Ser Glu Arg
 1               5                  10
```

( 2 ) INFORMATION FOR SEQ ID NO:5:

( i ) SEQUENCE CHARACTERISTICS:
        ( A ) LENGTH: 15 amino acids
        ( B ) TYPE: amino acid
        ( D ) TOPOLOGY: linear ( x i ) SEQUENCE DESCRIPTION: SEQ ID NO:5:

```
Phe Leu Ala Glu Glu Ala Asp Arg Lys Tyr Asp Glu Val Ala Arg
 1               5                  10                  15
```

( 2 ) INFORMATION FOR SEQ ID NO:6:

( i ) SEQUENCE CHARACTERISTICS:
        ( A ) LENGTH: 7 amino acids
        ( B ) TYPE: amino acid
        ( D ) TOPOLOGY: linear ( x i ) SEQUENCE DESCRIPTION: SEQ ID NO:6:

```
Lys Tyr Asp Glu Val Ala Arg
 1               5
```

( 2 ) INFORMATION FOR SEQ ID NO:7:

( i ) SEQUENCE CHARACTERISTICS:
        ( A ) LENGTH: 13 amino acids
        ( B ) TYPE: amino acid
        ( D ) TOPOLOGY: linear ( x i ) SEQUENCE DESCRIPTION: SEQ ID NO:7:

```
Ser Asn Gln Arg Glu Glu Glu Tyr Lys Asn Gln Ile Lys
 1               5                  10
```

( 2 ) INFORMATION FOR SEQ ID NO:8:

( i ) SEQUENCE CHARACTERISTICS:
        ( A ) LENGTH: 6 amino acids
        ( B ) TYPE: amino acid
        ( D ) TOPOLOGY: linear ( x i ) SEQUENCE DESCRIPTION: SEQ ID NO:8:

```
Ala Glu Phe Ala Glu Arg
 1               5
```

( 2 ) INFORMATION FOR SEQ ID NO:9:

( i ) SEQUENCE CHARACTERISTICS:
        ( A ) LENGTH: 17 amino acids
        ( B ) TYPE: amino acid
        ( D ) TOPOLOGY: linear ( x i ) SEQUENCE DESCRIPTION: SEQ ID NO:9:

```
Asp Gln Val Gln Glu Ser Leu Leu Lys Ala Asn Ile Gln Leu Val Glu
 1               5                  10                  15
Lys
```

( 2 ) INFORMATION FOR SEQ ID NO:10:

( i ) SEQUENCE CHARACTERISTICS:
        ( A ) LENGTH: 20 amino acids
        ( B ) TYPE: amino acid
        ( D ) TOPOLOGY: linear ( x i ) SEQUENCE DESCRIPTION: SEQ ID NO:10:

```
Asp Lys Ala Leu Ser Asn Ala Glu Gly Glu Val Ala Ala Leu Asn Arg
 1               5                  10                  15
Arg Ile Gln Leu
```

20

(2) INFORMATION FOR SEQ ID NO:11:

(i) SEQUENCE CHARACTERISTICS:
        (A) LENGTH: 15 amino acids
        (B) TYPE: amino acid
        (D) TOPOLOGY: linear (xi) SEQUENCE DESCRIPTION: SEQ ID NO:11:

```
Glu Glu Arg Ala Glu Thr Gly Glu Ser Lys Ile Val Glu Leu Glu
 1               5                  10                  15
```

(2) INFORMATION FOR SEQ ID NO:12:

(i) SEQUENCE CHARACTERISTICS:
        (A) LENGTH: 12 amino acids
        (B) TYPE: amino acid
        (D) TOPOLOGY: linear (xi) SEQUENCE DESCRIPTION: SEQ ID NO:12:

```
Asp Glu Leu Val Asn Glu Lys Glu Lys Tyr Lys Gln
 1               5                  10
```

(2) INFORMATION FOR SEQ ID NO:13:

(i) SEQUENCE CHARACTERISTICS:
        (A) LENGTH: 11 amino acids
        (B) TYPE: amino acid
        (D) TOPOLOGY: linear (xi) SEQUENCE DESCRIPTION: SEQ ID NO:13:

```
Arg Met Gln Gln Leu Glu Asn Asp Leu Asp Gln
 1               5                  10
```

(2) INFORMATION FOR SEQ ID NO:14:

(i) SEQUENCE CHARACTERISTICS:
        (A) LENGTH: 24 amino acids
        (B) TYPE: amino acid
        (D) TOPOLOGY: linear (xi) SEQUENCE DESCRIPTION: SEQ ID NO:14:

```
Ala Leu Ser Asn Ala Glu Gly Glu Val Ala Ala Leu Asn Arg Arg Ile
 1               5                  10                  15

Gln Leu Leu Glu Glu Asp Leu Glu
                20
```

(2) INFORMATION FOR SEQ ID NO:15:

(i) SEQUENCE CHARACTERISTICS:
        (A) LENGTH: 16 amino acids
        (B) TYPE: amino acid
        (D) TOPOLOGY: linear (xi) SEQUENCE DESCRIPTION: SEQ ID NO:15:

```
Ile Val Glu Leu Glu Glu Glu Leu Arg Val Val Gly Asn Asn Leu Lys
 1               5                  10                  15
```

(2) INFORMATION FOR SEQ ID NO:16:

(i) SEQUENCE CHARACTERISTICS:
        (A) LENGTH: 17 amino acids
        (B) TYPE: amino acid
        (D) TOPOLOGY: linear (xi) SEQUENCE DESCRIPTION: SEQ ID NO:16:

```
Ile Gln Thr Val Glu Asn Glu Leu Asp Gln Thr Gln Glu Ala Leu Thr
 1               5                  10                  15
```

Leu (2) INFORMATION FOR SEQ ID NO:17:

(i) SEQUENCE CHARACTERISTICS:
        (A) LENGTH: 9 amino acids
        (B) TYPE: amino acid
        (D) TOPOLOGY: linear (xi) SEQUENCE DESCRIPTION: SEQ ID NO:17:

```
Phe Leu Ala Glu Glu Ala Asp Lys Lys
1               5
```

(2) INFORMATION FOR SEQ ID NO:18:

(i) SEQUENCE CHARACTERISTICS:
        (A) LENGTH: 17 amino acids
        (B) TYPE: amino acid
        (D) TOPOLOGY: linear (xi) SEQUENCE DESCRIPTION: SEQ ID NO:18:

```
Leu Lys Gly Thr Glu Asp Glu Leu Asp Lys Tyr Ser Lys Ala Leu Lys
1               5                   10                  15
Asp
```

(2) INFORMATION FOR SEQ ID NO:19:

(i) SEQUENCE CHARACTERISTICS:
        (A) LENGTH: 9 amino acids
        (B) TYPE: amino acid
        (D) TOPOLOGY: linear (xi) SEQUENCE DESCRIPTION: SEQ ID NO:19:

```
His Ile Ala Glu Asp Ala Asp Arg Lys
1               5
```

(2) INFORMATION FOR SEQ ID NO:20:

(i) SEQUENCE CHARACTERISTICS:
        (A) LENGTH: 17 amino acids
        (B) TYPE: amino acid
        (D) TOPOLOGY: linear (xi) SEQUENCE DESCRIPTION: SEQ ID NO:20:

```
Leu Lys Gly Thr Glu Asp Glu Val Glu Lys Tyr Ser Lys Ser Val Lys
1               5                   10                  15
Asp
```

(2) INFORMATION FOR SEQ ID NO:21:

(i) SEQUENCE CHARACTERISTICS:
        (A) LENGTH: 9 amino acids
        (B) TYPE: amino acid
        (D) TOPOLOGY: linear (xi) SEQUENCE DESCRIPTION: SEQ ID NO:21:

```
His Ile Ala Glu Glu Ala Asp Arg Lys
1               5
```

(2) INFORMATION FOR SEQ ID NO:22:

(i) SEQUENCE CHARACTERISTICS:
        (A) LENGTH: 17 amino acids
        (B) TYPE: amino acid
        (D) TOPOLOGY: linear (xi) SEQUENCE DESCRIPTION: SEQ ID NO:22:

Leu Arg Ala Ser Glu Asp Glu Arg Asp Arg Val Leu Lys Glu Leu His
1               5                   10                  15

Lys (2) INFORMATION FOR SEQ ID NO:23:

(i) SEQUENCE CHARACTERISTICS:
        (A) LENGTH: 9 amino acids
        (B) TYPE: amino acid
        (D) TOPOLOGY: linear (xi) SEQUENCE DESCRIPTION: SEQ ID NO:23:

His Ile Ala Glu Glu Ser Asp Arg Lys
1               5

(2) INFORMATION FOR SEQ ID NO:24:

(i) SEQUENCE CHARACTERISTICS:
        (A) LENGTH: 285 amino acids
        (B) TYPE: amino acid
        (D) TOPOLOGY: linear (xi) SEQUENCE DESCRIPTION: SEQ ID NO:24:

Met Asp Ala Ile Lys Lys Lys Met Gln Ala Met Lys Asx Asp Lys Asp
1               5                   10                  15

Gly Ala Leu Glu Arg Ala Leu Asx Cys Glu Gln Glu Ala Arg Asp Ala
                20                  25                  30

Asn Thr Arg Ala Glu Lys Ala Glu Glu Ala Arg Gln Leu Gln Lys
            35                  40                  45

Lys Ile Gln Thr Val Glu Asn Glu Leu Asp Gln Thr Gln Glu Ala Leu
    50                  55                  60

Thr Leu Val Thr Gly Lys Leu Glu Glu Lys Asn Lys Ala Leu Gln Asn
65                  70                  75                  80

Ala Glu Ser Glu Val Ala Ala Leu Asn Arg Arg Ile Gln Leu Leu Glu
                85                  90                  95

Glu Asp Leu Glu Arg Ser Glu Glu Arg Leu Gly Ser Ala Thr Ala Lys
                100                 105                 110

Leu Ser Glu Ala Ser Gln Ala Ala Asp Glu Ser Glu Arg Ala Arg Lys
            115                 120                 125

Ile Leu Glu Asn Arg Ala Leu Ala Asp Glu Glu Arg Met Asp Ala Leu
            130                 135                 140

Glu Asn Gln Leu Lys Glu Ala Arg Phe Leu Ala Glu Glu Ala Asp Lys
145                 150                 155                 160

Lys Tyr Asp Glu Val Ala Arg Lys Leu Ala Met Val Glu Ala Asp Leu
                165                 170                 175

Glu Arg Ala Glu Glu Arg Ala Glu Gln Gly Glu Asn Lys Ile Val Glu
                180                 185                 190

Leu Glu Glu Glu Leu Arg Val Val Gly Asn Asn Leu Lys Ser Leu Glu
            195                 200                 205

Val Ser Glu Glu Lys Ser Asn Gln Arg Glu Glu Glu Tyr Lys Asn Gln
            210                 215                 220

Ile Lys Thr Leu Asn Thr Arg Leu Lys Glu Ala Glu Ala Arg Ala Glu
225                 230                 235                 240

Phe Ala Glu Arg Ser Val Gln Lys Leu Gln Lys Glu Val Asp Arg Leu
                245                 250                 255

Glu Asp Asp Leu Val Leu Glu Lys Glu Arg Tyr Lys Asp Ile Gly Asp
            260                 265                 270

Asp Leu Asp Thr Ala Phe Val Glu Leu Ile Leu Lys Glu
            275                 280                 285

-continued

What is claimed is:

1. A peptide selected from the group consisting of FLAEEADRK, MQQLENDLDQVQESLLK, fragments and muteins of FLAEEADRK and MQQLENDLDQVOESLLK, and larger molecules that consist essentially of FLAEEADRK or MQQLENDLDQVQESLLK and can safely desensitize individuals to tropomyosin allergen without causing a severe adverse reaction, said fragments, muteins and larger molecules having allergenic activity such that they evoke a positive skin reaction in a patient sensitive to ingestion of crustaceans.

2. A peptide according to claim 1, wherein said variant inhibits the binding to crustacea tropomyosin of crustacea tropomyosin-specific IgE antibodies.

3. A peptide according to claim 2, wherein said crustacea tropomyosin-specific IgE antibodies are shrimp tropomyosin-specific IgE antibodies and said crustacea tropomyosin is shrimp tropomyosin.

4. A peptide according to claim 2, wherein said crustacea tropomyosin-specific IgE antibodies are obtained from sera of a subject having a positive skin-prick test reaction to said crustacea tropomyosin.

5. A peptide according to claim 3, wherein said shrimp tropomyosin-specific IgE antibodies are obtained from sera of a subject having a positive skin-prick test reaction to shrimp tropomyosin.

6. A peptide according to claim 2, wherein said variant inhibits the binding to crustacea tropomyosin of said crustacea tropomyosin-specific IgE antibodies by at least 45%.

7. A peptide according to claim 1, wherein said peptide is FLAEEADRK (SEQ ID NO: 1) or a variant thereof having allergenic activity.

8. A peptide according to claim 1, wherein said peptide is FLAEEADRK (SEQ ID NO: 1).

9. A peptide according to claim 1, wherein said peptide is MQQLENDLDQVQESLLK (SEQ ID NO: 2) or a variant thereof having allergenic activity.

10. A peptide according to claim 1, wherein said peptide is MQQLENDLDQVQESLLK (SEQ ID NO: 2).

11. A peptide selected from the group consisting of FLAEEADRK and MQQLENDLDQVQESLLK, and muteins thereof.

12. A peptide according to claim 11, wherein said peptide is a mutein that inhibits the binding to crustacea tropomyosin of crustacea tropomyosin-specific IgE antibodies by at least 45%.

13. A peptide according to claim 12, wherein said crustacea tropomyosin-specific IgE antibodies are shrimp tropomyosin-specific IgE antibodies and said crustacea tropomyosin is shrimp tropomyosin.

14. A peptide according to claim 12, wherein said peptide is a mutein of FLAEEADRK.

15. A peptide according to claim 12, wherein said peptide is a mutein of MQQLENDLDQVQESLLK.

16. A peptide according to claim 1, wherein said peptide is a fragment of FLAEEADRK or a fragment of MQQLENDLDQVQESLLK, in which one or more amino acids, exclusive of amino acids F and L of FLAEEADRK, are truncated.

17. A peptide according to claim 1, wherein said peptide has an homology of at least 70% with one of FLAEEADRK and MQQLENDLDQVQESLLK.

18. A peptide according to claim 1 including a region that is homologous with a peptide selected from the group consisting of FLAEEADRK and MQQLENDLDQVQESLLK, wherein said peptide evokes a positive skin reaction in a patient sensitive to ingestion of crustaceans.

19. A peptide according to claim 18, wherein said peptide inhibits the binding to crustacea tropomyosin of crustacea tropomyosin-specific IgE antibodies by at least 45%.

20. A peptide according to claim 19, wherein said region is at least 70% homologous with one of FLAEEADRK and MQQLENDLDQVQESLLK.

* * * * *